April 16, 1940. A. DICKSON, JR Plant Pat. 376
ROSE PLANT
Filed June 1, 1939
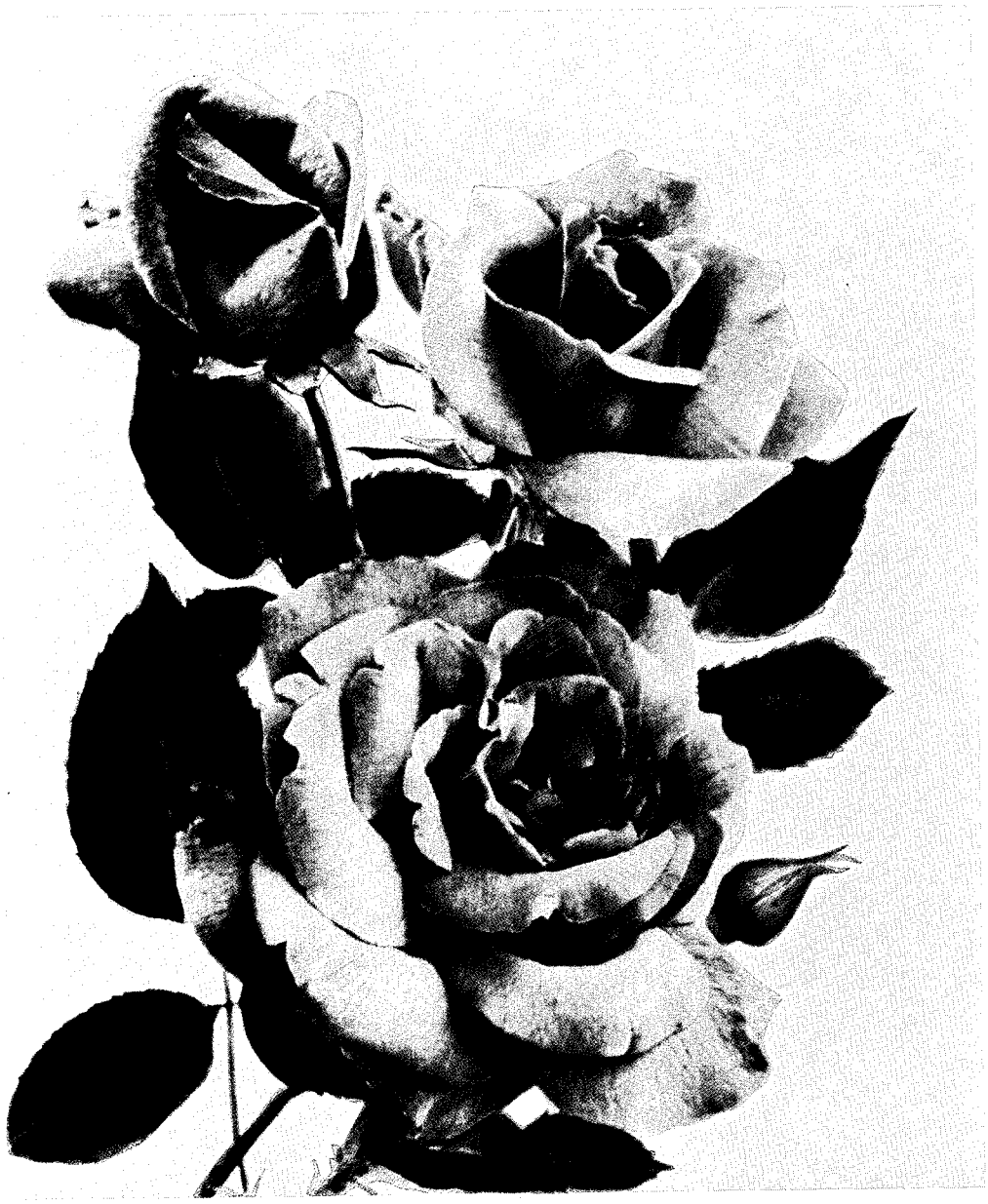
Inventor
A. Dickson, Jr
By Robb & Robb
attorneys Patented Apr. 16, 1940

Plant Pat. 376

UNITED STATES PATENT OFFICE

376

ROSE PLANT

Alexander Dickson, Jr., Newtonards, Belfast, Ireland, assignor to Jackson & Perkins Company, Newark, N. Y.

Application June 1, 1939, Serial No. 276,917

1 Claim. (Cl. 47—61)

This invention relates to a new and distinct variety of Hybrid Tea Rose plant, a seedling resulting from a cross of unnamed seedling parents.

The novel characteristics of this new rose reside primarily in the flower, and especially its color—Carmine with a velvety overcast of Ox Blood Red on the inside of the petals and shiny Bordeaux shading to Pomegranate Purple on the outside. In the bud, the color is velvety Bordeaux (Bordeaux with velvety sheen) when the sepals first divide. The petal arrangement is informal with the three outside petals somewhat the shorter and deeply cleft.

These flowers are borne on individual, long stems. Importantly, the new variety is valued for the persistency of its blooming and its resistance to heat.

Other marks of distinction of this rose are found in the coloring of the young foliage of the plant, the form and color of its thorns and prickles as well as the sharp persistent fragrance of the flowers.

The new rose has been asexually reproduced and found to come true to form.

The following is a detailed description of the new variety, the color terminology being in accord with Ridgway's Color Standard.

Parentage:

*Seed parent.*—Unnamed (Richmond × unnamed seedling).

*Pollen parent.*—Unnamed seedling.

Classification:

*Botanic.*—Hybrid Tea.

*Commercial.*—Hybrid Tea.

*Flower*

Blooming habit:

Observations made in the morning of June 30, 1938, at Newark, New York.

Blooms in the fall.

*Recurrent.*—Continuous.

Bud:

*Size.*—Medium.

*Form.*—Long. Unaffected by wet or hot weather.

*Color.*—When sepals first divide—Velvety Bordeaux, Plate 12. When petals begin to unfurl—Ox Blood Red, Plate 1, suffused with Carmine, Plate 1. When petals half blown: inside of petals—Carmine, Plate 1, with overcast of Ox Blood Red, Plate 1; reverse of petals—between Bordeaux, Plate 12, and Pomegranate Purple, Plate 12.

*Sepals.*—Branched, "hood" above bud. Curl back when half open.

*Calyx.*—Shape—funnel. Size—small, slender. Aspect—smooth.

*Peduncle.*—Length—long. Aspect—smooth. Color—Cress Green, Plate 31. Strength—stiff, erect, slender.

*Opening.*—Bud opens well. Is not affected by adverse conditions.

Bloom:

*Size.*—Large. Average size when fully expanded—4"-5".

*Borne.*—Several together.

*Stems.*—Medium length, strong.

*Form.*—When first open—globular. Permanance—outer petals curl back slightly.

*Petalage.*—Double (full but open center). Many petals and stamens hidden. Number of petals under normal conditions—35.

*Color.*—Center of flower—between Carmine, Plate 1, and Ox Blood Red, Plate 1, with velvety overcast. Outer petals—Carmine, Plate 1, with velvety overcast of Ox Blood Red, Plate 1. Base of petals (aiglet), very small—Straw Yellow, Plate 16. Inside of petals—Carmine, Plate 1, with velvety overcast of Ox Blood Red, Plate 1. Reverse of petals—between Bordeaux, Plate 12, and Pomegranate Purple, Plate 12. General tonality from a distance—Deep Velvety Red (general color terminology).

*Discoloration.*—At end of first day—Ox Blood Red, Plate 1. Second day—Carmine, Plate 1. Third day—Carmine, Plate 1.

Petals:

*Texture.*—Thick. Unaffected by wet or hot weather.

*Appearance.*—Inside—velvety. Outside—shiny.

*Form.*—Oval, scalloped.

*Arrangement*—Informal (with "rags" in center). Three outside petals shorter and deeply cleft and three inside petals similar.

*Persistence.*—Drop off cleanly.

*Fragrance.*—Strong. Nature—fruity (Russet apple). Other fragrance—a sharp persistent fragrance.

*Lasting quality.*—On plant and as cut flower—long.

Genital organs:

*Stamens, anthers.*—Many. Color—Primuline Yellow, Plate 16. Arrangement—regular around styles.

*Stamens, filaments (threads).*—Medium length. Color—Ox Blood Red, Plate 1.

*Pollen.*—Wax Yellow, Plate 16.

*Styles.*—Bunched, medium length, thin.

*Stigmas.*—Color—Straw Yellow, Plate 16.
*Ovaries.*—All enclosed in calyx.
Fruit: Variety is fertile with its own pollen.

*Plant*

Form: Bush.
Growth: Vigorous, branching, compact.
Foliage: Number of leaflets—3–5.
*Size.*—Large.
*Quantity.*—Abundant.
*Color.*—New foliage: center—Dark Cress Green, Plate 31, and mid-rib and edge—Hay's Maroon, Plate 13; under side—Mineral Red, Plate 27. Old foliage: upper side—Yew Green, Plate 31; under side—Light Cress Green, Plate 31.
*Shape.*—Oval pointed.
*Texture.*—Upper side—leathery, smooth. Under side—rough. Ribs and veins—prominent.
*Edge.*—Serrated (saw toothed).
*Serration.*—Single, small.
*Rachis.*—Color—Cress Green, Plate 31. Under side—smooth.
*Stipules.*—Medium length, bearded.
*Disease resistance.*—Resistant.

Wood:
*New wood.*—Color—Mineral Red, Plate 27. Bark—smooth.
*Old wood.*—Color—Cress Green, Plate 31. Bark—smooth.

Thorns (thorns are divided into thorns, prickles and short needles):
*Thorns.*—Quantity: on main stalks from base—few; on laterals from stalk—none. Form—narrow base, medium length, hooked downward. Color when young—Hessian Brown, Plate 13. Position—irregular.
*Prickles.*—On main stalks—few. On laterals—few. Color—Hessian Brown, Plate 13.
*Short needles.*—Quantity: on main stalks—few; on laterals—few.

I claim:

A new and distinctive variety of Hybrid Tea Rose plant, characterized as to novelty by the deep rich coloring of its flowers, the arrangement and form of the petals thereof, and the persistent blooming heat resistant habit of growth, substantially as shown and described.

ALEXANDER DICKSON, JR.